United States Patent [19]

Hopp et al.

[11] Patent Number: 5,475,169
[45] Date of Patent: Dec. 12, 1995

[54] PROCESS FOR THE REMOVAL OF OLEFINIC IMPURITIES FROM 1,1,1,2,3,3,3-HEPTAFLUOROPROPANE

[75] Inventors: Peter Hopp, Hofheim; Rolf-Michael Jansen, Kelkheim, both of Germany

[73] Assignee: Hoechst AG, Frankfurt, Germany

[21] Appl. No.: 879,810

[22] Filed: May 7, 1992

[30] Foreign Application Priority Data

May 8, 1991 [DE] Germany .......................... 41 15 025.2

[51] Int. Cl.$^6$ .................................................. C07C 17/38
[52] U.S. Cl. ............................................................ 570/178
[58] Field of Search ............................................. 570/178

[56] References Cited

U.S. PATENT DOCUMENTS

| | | | |
|---|---|---|---|
| 2,409,274 | 10/1946 | Hanford et al. | 260/614 |
| 4,973,774 | 11/1990 | Rozen et al. | 570/178 |
| 5,118,873 | 6/1992 | Smith | 568/697 |

FOREIGN PATENT DOCUMENTS

| | | |
|---|---|---|
| 0370688 | 5/1990 | European Pat. Off. . |
| 1219460 | 6/1966 | Germany ................ 570/178 |
| 902590 | 8/1962 | United Kingdom . |
| 1031409 | 6/1966 | United Kingdom . |

OTHER PUBLICATIONS

Chemical Abstract, vol. 71, 60600w, "Fluoroolefins IV., Base-catalyzed reactions of fluoropropylenes with alcohols. Stearochemical aspects of the reactions", 1969, pp. 366–367.
Lovelaee et al Aliphatic Fluorine Comp (1958) pp. 156, 157.
Chem Abst. (1971) vol. 13: 60600w.

*Primary Examiner*—Alan Siegel
*Attorney, Agent, or Firm*—Connolly & Hutz

[57] ABSTRACT

Process for the removal of olefinic impurities from 1,1,1,2,3,3,3-heptafluoropropane The invention relates to a process for the removal of olefinic impurities from 1,1,1,2,3,3,3-heptafluoropropane (R 227) in which the contaminated R 227 is brought into contact with an alcohol and a base, and the R 227 is simultaneously or subsequently removed by distillation.

17 Claims, No Drawings

PROCESS FOR THE REMOVAL OF OLEFINIC IMPURITIES FROM 1,1,1,2,3,3,3-HEPTAFLUOROPROPANE

DESCRIPTION

Process for the removal of olefinic impurities from 1,1,1,2,3,3,3-heptafluoropropane The invention relates to a process for the removal of olefinic impurities from 1,1,1,2,3,3,3-heptafluoropropane (R 227), the preparation of which is disclosed in British Patent 902,590. This compound has been proposed as a substitute for ozone-endangering, fully halogenated chlorofluorocarbons. In order to be able to use R 227 in refrigeration or as a propellant for pharmaceutical aerosols, interfering and toxic olefinic impurities formed during synthesis—in some cases only trace amounts—must be removed completely. This is not possible within economically acceptable limits by means of conventional physical methods such as distillation or adsorption. It is therefore necessary to find another way of converting the interfering impurities, by reaction with suitable substances, into nontoxic compounds or into those which can be separated from R 227 by physical means without great expense.

It has proven favorable to react the olefins, such as 2H-pentafluoropropene, formed in the preparation of R 227, with alcohols in the presence of bases. This forms exclusively high-boiling compounds, which can easily be separated from R 227 during purification distillation. In addition, R 227 is not attacked, and the reaction proceeds quickly and quantitatively.

Although it is disclosed in Chemical Abstracts 1971, Vol. 13: 60600 w that a mixture of relatively high-boiling ethers and esters can be prepared from 2H-pentafluoropropene and alcohols in the presence of KOH, the conversions are not quantitative. It could therefore not have been expected that traces of 2H-pentafluoropropene and other olefins, dissolved in R 227, can be removed quantitatively by reaction with alcohols. In addition, it was feared that R 227 would form azeotropes with alcohols, analogously to many other fluorinated hydrocarbons.

The invention relates to a process for the removal of olefinic impurities of the formula $C_nH_mF_pCl_q$ wherein n=2–6, m=0–8, p=1–12, q=0–8 and m+p+q=2n, from 1,1,1,2,3,3,3-heptafluoropropane (R 227), which comprises bringing the contaminated R 227 into contact with an alcohol and a base at temperatures of from −20° to 100° C. and at pressures of from 1 to 50 bar, and simultaneously or subsequently removing the R 227 by distillation.

The impurities are in particular 1,1,3,3,3-pentafluoropropene (2H-pentafluoropropene) and perfluoropropene.

It is preferred to use a monohydric alcohol of the formula $C_aH_{2a+1}OH$, $C_aH_{2a}(OH)_2$, $C_aH_{2a-1}OH$ or $C_aH_{2a-2}$ where a=1 to 6, in particular 1 to 3. Particularly suitable are methanol, ethanol, i-propanol and ethylene glycol (glycol).

The bases used are preferably those whose pK is from 8 to 14, in particular NaOH, KOH or sodium phenoxide.

The temperature is preferably from 0° to 50° C. and the pressure is preferably from 1 to 10 bar. Based on R 227, the amount of alcohol is preferably from 0.5 to 10% by weight and the amount of base is preferably from 0.01 to 5% by weight.

The invention is illustrated in greater detail with reference to the examples below.

EXAMPLES 1 TO 9

A heatable stirred autoclave (V=300 ml) was charged with 100 g of 1,1,1,2,3,3,3-heptafluoropropane (R 227) containing about 500 ppm of 2H-pentafluoropropene (PFP), and with 10 g of an alcohol and 1 g of a base. The autoclave was subsequently warmed to 50° C. (pressure 9.3 bar) and stirred at this temperature for 4 hours. The content of PFP was monitored by gas chromatography. The alcohols and bases employed and the results are shown in Table 1.

TABLE 1

| Alcohol | Base | Content of PFP [ppm] after 4 hours |
|---|---|---|
| Methanol | NaOH | b.d.l.* |
| Methanol | KOH | b.d.l.* |
| Methanol | Sodium acetate | 350 |
| Methanol | $Na_2HPO_3$ | 400 |
| Methanol | Pyridine | 280 |
| Methanol | Sodium phenoxide | 150 |
| Ethanol | NaOH | b.d.l.* |
| i-Propanol | NaOH | 30 |
| Glycol | NaOH | b.d.l.* |

*b.d.l. = below detection limit (<1 ppm)

EXAMPLE 10

A distillation vessel was charged with 80 kg of R 227 containing about 200 ppm of 2H-pentafluoropropene, and with 600 g of methanol and 15 g of KOH. The vessel was subsequently warmed to 30° C. and stirred at this temperature for 12 hours. The content of PFP had dropped to less than 10 ppm.

We claim:

1. A process for the removal of olefinic impurities of the formula $C_nH_mF_p$ from wherein n=2–6, m=0–8, p=1–12, and m+p=2n, from 1,1,1,2,3,3,3-heptafluoropropane (R 227) which comprises bringing the contaminated R227 into contact with an alcohol and a base at a temperature of from −20° to 100° C. and at a pressure of from 1 to 50 bar, and simultaneously or subsequently removing the R227 by distillation.

2. The process as claimed in claim 1, wherein an alcohol of the formula $C_nH_{2n+1}OH$, $C_nH_{2n}(OH)_2$, $C_nH_{2n-1}OH$ or $C_nH_{2n-2}(OH)_2$ were n=1–6 is used.

3. The process as claimed in claim 1, wherein a base is used whose pK is from 8 to 14.

4. The process as claimed in claim 1, wherein the process is carried out at from 0° to 50° C. and at from 1 to 10 bar.

5. The process as claimed in claim 1, wherein the alcohol used is ethylene glycol, methanol, ethanol or i-propanol.

6. The process as claimed in claim 1, wherein the base used is NaOH, KOH or sodium phenoxide.

7. The process as claimed in claim 1, wherein from 0.5 to 10% by weight of alcohol and from 0.01 to 5% by weight of base are used, based on R 227.

8. The process as claimed in claim 2, wherein n is 1 to 3.

9. The process as claimed in claim 1, wherein the temperature is from 0 to 50° C. and the pressure is from 1 to 10 bar.

10. The process as claimed in claim 1, wherein the impurities are 1,1,3,3,3-pentafluoropropene and perfluoropropene.

11. The process as claimed in claim 1, wherein the base is NaOH or KOH.

12. The process as claimed in claim 11, wherein the base is NaOH.

13. The process as claimed in claim 11, wherein the alcohol is methanol.

14. The process as claimed in claim 1, wherein 30 ppm or less of 1,1,3,3,3-pentafluoropropene remains in the R227.

15. The process as claimed in claim 1, wherein less than 1 ppm of 1,1,3,3,3-pentafluoropropene remains in the R227.

16. A process for the removal of 1,1,3,3,3-pentafluoropropene or perfluoropropene from 1,1,1,2,3,3,3-heptafluoropropane (R 227) which comprises bringing the contaminated R227 into contact with an alcohol and a base, wherein said base is either NaOH or KOH, at a temperature of from −20° to 100° C. and at a pressure of from 1 to 50 bar, and simultaneously or subsequently removing the R227 by distillation.

17. A process for the removal of impurities consisting essentially of 1,1,3,3,3-pentafluoropropene or perfluoropropene from 1,1,1,2,3,3,3-heptafluoropropane (R 227) which comprises bringing the R227 contaiminated with 1,1,3,3,3-pentafluoropropene or perfluoropropene into contact with an alcohol and a base, wherein said base is either NaOH or KOH, at a temperature of from −20° to 100° C. and at a pressure of from 1 to 50 bar, and simultaneously or subsequently removing the R227 by distillation.

* * * * *